(12) United States Patent
Vaccaro et al.

(10) Patent No.: US 7,762,120 B2
(45) Date of Patent: Jul. 27, 2010

(54) TAPERED ULTRASONIC REFERENCE STANDARD

(75) Inventors: Christopher M. Vaccaro, Ofallon, MO (US); April L. Beisiegel, Freeburg, IL (US); David A. Lilienthal, Kent, WA (US)

(73) Assignee: The Boeing Company, Chicago, IL (US)

( * ) Notice: Subject to any disclaimer, the term of this patent is extended or adjusted under 35 U.S.C. 154(b) by 1061 days.

(21) Appl. No.: 11/292,916

(22) Filed: Dec. 1, 2005

(65) Prior Publication Data
US 2007/0125177 A1  Jun. 7, 2007

(51) Int. Cl.
*G01N 29/30* (2006.01)
(52) U.S. Cl. ...................................................... 73/1.86
(58) Field of Classification Search .................. 73/1.82, 73/1.86
See application file for complete search history.

(56) References Cited

U.S. PATENT DOCUMENTS

| | | | |
|---|---|---|---|
| 3,784,043 A | | 1/1974 | Presnick |
| 3,908,439 A | * | 9/1975 | Pelak et al. ................... 73/1.86 |
| 3,933,026 A | | 1/1976 | Ham |
| 4,156,123 A | | 5/1979 | Fischer et al. |
| 4,173,139 A | * | 11/1979 | Conn .......................... 73/1.84 |
| 4,266,154 A | | 5/1981 | Marshall |
| 4,393,987 A | | 7/1983 | Anderson et al. |
| 4,406,153 A | | 9/1983 | Ophir et al. |
| 4,445,360 A | | 5/1984 | Treder, Jr. |
| 4,466,270 A | | 8/1984 | Kimura et al. |
| 4,566,330 A | * | 1/1986 | Fujii et al. ..................... 73/599 |
| 4,575,330 A | * | 3/1986 | Hull ......................... 425/174.4 |
| 4,660,419 A | | 4/1987 | Derkacs |
| 4,674,334 A | | 6/1987 | Chimenti et al. |
| 4,729,235 A | | 3/1988 | Podlech |
| 4,747,295 A | * | 5/1988 | Feist et al. .................... 73/1.86 |
| 4,779,452 A | | 10/1988 | Cohen-Tenoudji |
| 5,054,310 A | | 10/1991 | Flynn |
| 5,065,520 A | | 11/1991 | Shimizu et al. |
| RE33,789 E | | 1/1992 | Stevenson |
| 5,127,268 A | | 7/1992 | Kline |
| 5,163,027 A | * | 11/1992 | Miller et al. ................... 367/13 |
| 5,163,077 A | | 11/1992 | Dupre |

(Continued)

FOREIGN PATENT DOCUMENTS

DE          28 14 3 36 B1     5/1979

(Continued)

OTHER PUBLICATIONS

European Patent Office (International Searching Authority) PCT/US2007/086465 International Search Report/Written Opinion, Jun. 30, 2008.

Primary Examiner—Hezron Williams
Assistant Examiner—Rose M Miller
(74) Attorney, Agent, or Firm—Klintworth & Rozenblatt IP LLC

(57) ABSTRACT

The invention relates to tapered reference standards, and methods for their manufacture and use. An ultrasonic inspection reference standard for tapered, composite materials may include a member having at least one tapered section. The member may be manufactured from a fiber-free polymer resin using a stereo lithography process. The tapered reference standards may substantially mimic the affect on ultrasonic sound passing through tapered sections in composite laminates.

34 Claims, 11 Drawing Sheets
(2 of 11 Drawing Sheet(s) Filed in Color)

U.S. PATENT DOCUMENTS

| | | | |
|---|---|---|---|
| 5,196,343 A | | 3/1993 | Zerhouni et al. |
| 5,238,556 A | | 8/1993 | Shirkhan |
| 5,312,755 A | | 5/1994 | Madsen et al. |
| 5,525,385 A | | 6/1996 | Weinstein et al. |
| 5,551,881 A | * | 9/1996 | Henderson et al. .......... 434/299 |
| 5,603,797 A | | 2/1997 | Thomas et al. |
| 5,637,175 A | | 6/1997 | Feygin et al. |
| 5,656,763 A | | 8/1997 | Flax |
| 5,662,566 A | * | 9/1997 | Marxrieser et al. .............. 483/1 |
| 5,837,880 A | * | 11/1998 | Shakinovsky et al. ........ 73/1.86 |
| 6,238,343 B1 | | 5/2001 | Madsen et al. |
| 6,364,986 B1 | | 4/2002 | Kieronski |
| 6,405,583 B1 | | 6/2002 | Shirakawabe et al. |
| 6,415,051 B1 | | 7/2002 | Callari et al. |
| 6,415,644 B1 | * | 7/2002 | Rockwood et al. ........... 73/1.86 |
| 6,426,274 B1 | | 7/2002 | Tayanaka |
| 6,635,112 B1 | * | 10/2003 | Choy et al. ................. 118/620 |
| 6,649,516 B2 | | 11/2003 | Asakawa et al. |
| 6,684,701 B2 | | 2/2004 | Dubois et al. |
| 6,803,095 B1 | | 10/2004 | Halladay et al. |
| 6,843,945 B1 | | 1/2005 | Lee et al. |
| 6,925,145 B2 | | 8/2005 | Batzinger |
| 6,959,602 B2 | | 11/2005 | Peterson et al. |
| 6,962,701 B2 | | 11/2005 | Koenig |
| 6,962,739 B1 | | 11/2005 | Kim et al. |
| 7,010,980 B2 | | 3/2006 | Meier |
| 7,076,992 B2 | * | 7/2006 | Greelish ..................... 73/1.86 |
| 7,188,559 B1 | | 3/2007 | Vecchio |
| 7,216,544 B2 | * | 5/2007 | Vaccaro et al. ................. 73/620 |
| 7,320,241 B2 | * | 1/2008 | Kollgaard et al. ............. 73/1.86 |
| 7,353,709 B2 | | 4/2008 | Kruger et al. |
| 7,357,014 B2 | | 4/2008 | Vaccaro et al. |
| 7,418,860 B2 | | 9/2008 | Austerlitz et al. |
| 7,424,818 B2 | | 9/2008 | Vaccaro et al. |
| 7,509,832 B2 | * | 3/2009 | Vaccaro et al. ................ 73/1.86 |
| 7,510,817 B2 | | 3/2009 | Benoit et al. |
| 2003/0086535 A1 | * | 5/2003 | Teppaz et al. ................ 378/207 |
| 2006/0213250 A1 | | 9/2006 | Vaccaro et al. |
| 2006/0234391 A1 | | 10/2006 | Weiss et al. |
| 2006/0265679 A1 | | 11/2006 | Scheffer et al. |
| 2007/0089479 A1 | * | 4/2007 | Vaccaro et al. ................ 73/1.86 |
| 2007/0101815 A1 | * | 5/2007 | Kollgaard et al. ............. 73/618 |
| 2007/0107520 A1 | * | 5/2007 | Vaccaro et al. ................ 73/649 |
| 2007/0125177 A1 | | 6/2007 | Vaccaro et al. |
| 2008/0087093 A1 | * | 4/2008 | Engelbart et al. ............. 73/620 |
| 2008/0121039 A1 | | 5/2008 | Vaccaro et al. |
| 2008/0134749 A1 | * | 6/2008 | Engelbart et al. ............ 73/1.86 |
| 2008/0196475 A1 | * | 8/2008 | Engelbart et al. ............ 73/1.86 |

FOREIGN PATENT DOCUMENTS

| | | |
|---|---|---|
| GB | 2221991 A | 2/1990 |
| JP | 61-265565 | 11/1986 |
| JP | 08210953 A | 8/1996 |
| WO | 90/13024 A1 | 11/1990 |

* cited by examiner

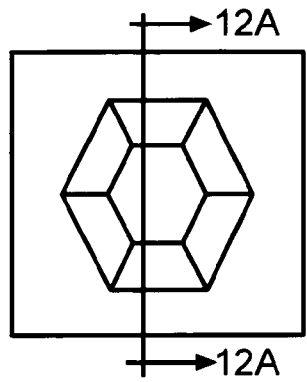 
FIG. 12     FIG. 12A
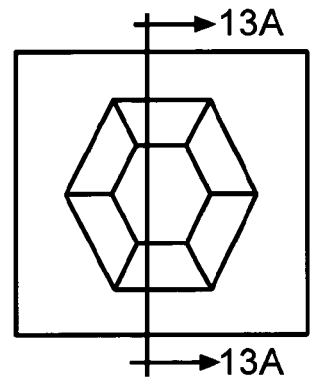 
FIG. 13     FIG. 13A
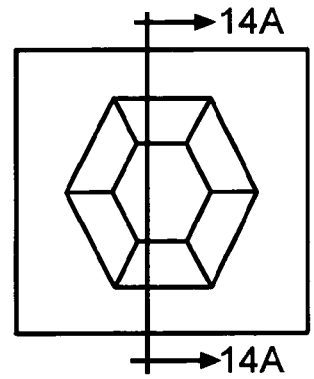 
FIG. 14     FIG. 14A

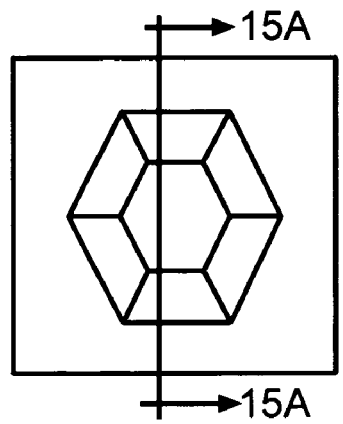
FIG. 15    FIG. 15A
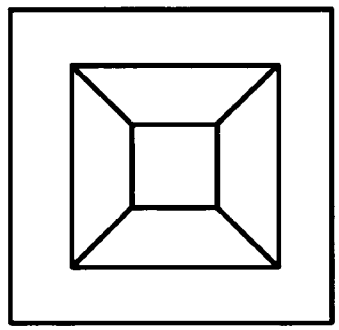
FIG. 16

TAPERED ULTRASONIC REFERENCE STANDARD

CROSS-REFERENCE TO RELATED APPLICATIONS

This application hereby incorporates by reference U.S. application Ser. No. 11/090,553, filed on Mar. 25, 2005, and titled Ultrasonic Inspection Reference Standard For Composite Materials.

BACKGROUND OF THE INVENTION

Composite laminate reference standards are employed when performing ultrasonic inspection of composite laminate materials. They are used to aid in the detection of defects such as delaminations, foreign material, and the detection and quantification of porosity. A relationship exists between the strength of a composite laminate and the presence of defect conditions. This relationship is established in the course of effects-of-defects programs that look at the strength degradation of materials as a result of defects. Composite reference standards are currently manufactured with representative conditions to aid in the detection of delaminations and foreign material. However, it may be difficult to manufacture reference standards, which are adapted to tie detection and quantification of defects in tapered, composite parts. A reference standard, and method for its manufacture and use, is needed for the inspection of tapered, composite parts.

SUMMARY OF THE INVENTION

In one aspect of the invention, an ultrasonic inspection reference standard for composite materials, having at least one first tapered section, comprises a member having at least one second tapered section. The member is manufactured from a fiber-free polymer resin.

In another aspect of the invention, an ultrasonic inspection process for tapered composite materials is disclosed. The process comprises the steps of manufacturing a reference standard, and inspecting a fiber-reinforced composite part, having at least one second tapered section, with an ultrasonic technique using the reference standard. The reference standard comprises a member having at least one first tapered section.

In a further aspect of the invention, a process for manufacturing an ultrasonic reference standard for tapered composite materials is disclosed. The process comprises the steps of creating a model of an ultrasonic inspection standard having a first tapered section, and manufacturing a reference standard having a second tapered section based on the model.

These and other features, aspects and advantages of the invention will become better understood with reference to the following drawings, description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12 depicts a top view of an embodiment of a single taper reference standard under the invention;

FIG. 12A depicts a partial cross-sectional view along line 12A in the embodiment shown in FIG. 12;

FIG. 13 depicts a top view of another embodiment of a single taper reference standard under the invention;

FIG. 13A depicts a partial cross-sectional view along line 13A in the embodiment shown in FIG. 13;

FIG. 14 depicts a top view of an embodiment of a dual taper reference standard under the invention;

FIG. 14A depicts a partial cross-sectional view along line 14A in the embodiment shown in FIG. 14;

FIG. 15 depicts a top view of another embodiment of a dual taper reference standard under the invention;

FIG. 15A depicts a partial cross-sectional view along line 15A in the embodiment shown in FIG. 15; and FIG. 16 depicts a top view of another embodiment of a reference standard under the invention, which may have a single or dual taper.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Generally, this invention discloses the use and manufacture of tapered ultrasonic inspection reference standards for analyzing and inspecting the strength of composite laminates having tapered regions.

Composite laminate reference standards may be utilized when performing ultrasonic inspection to establish the bulk attenuation properties for a pristine material. However, the production of composite laminate reference standards may be costly, inaccurate, and inefficient. Previous work has shown that photo-polymer resins used in stereo lithography (SLA), as well as conventional thermo set and thermoplastic resins like those used to bind fibers in composite laminates, have similar ultrasonic (acoustic) properties to graphite epoxy composite laminates. This is detailed in U.S. application Ser. No. 11/090,553, filed on Mar. 25, 2005, and titled Ultrasonic Inspection Reference Standard For Composite Materials, which is hereby incorporated by reference. The use of SLA on photo-polymer resins, and other resins, may produce reference standards more efficiently, less expensively, and/or more accurately than previous reference standards.

Figure 1:
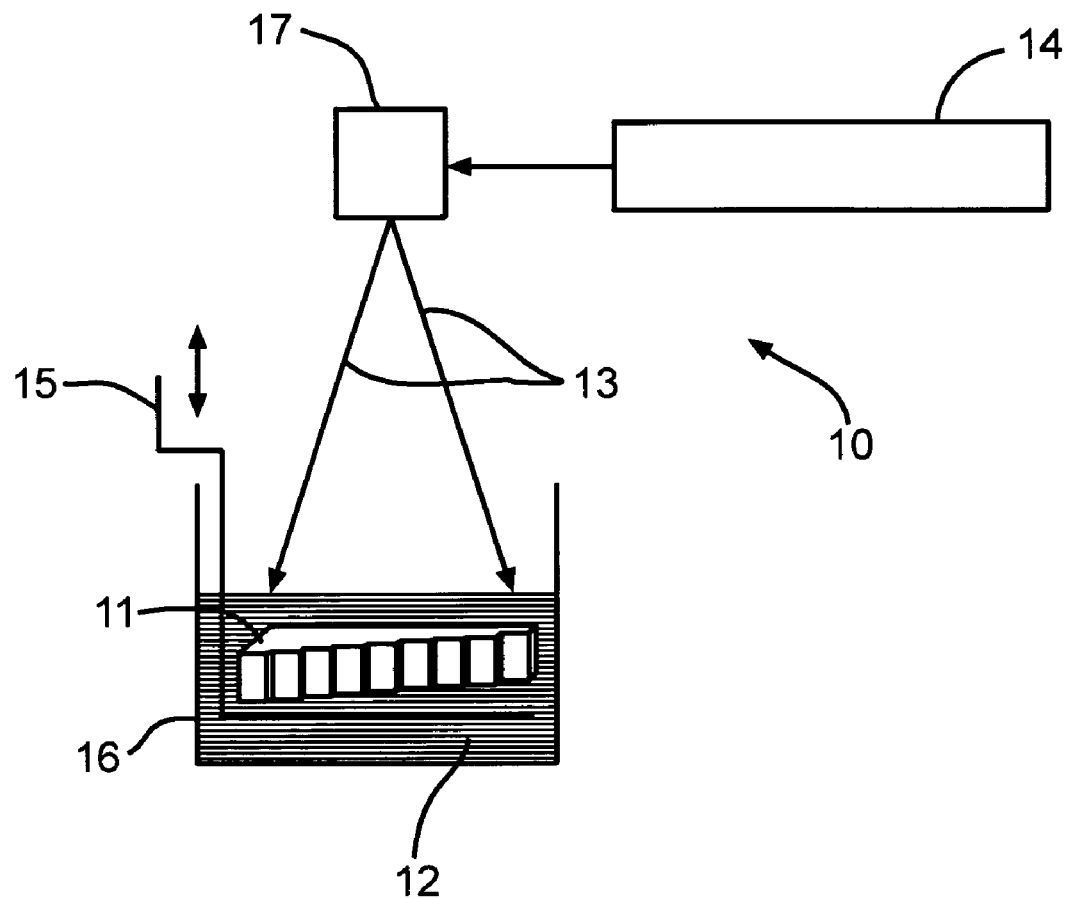
FIG. 1 is a front view of a stereo lithography process.

As shown in FIG. 1, the use of a stereo lithography process 10 may produce plastic parts 11, such as an ultrasonic inspection reference standard manufactured from a photo-polymer resin, directly from a 3D CAD (computer-aided design) model. The surface of a liquid photopolymer 12 is solidified layer-by-layer using a laser beam 13 emitted by a laser 14. When the laser beam 13 hits the liquid photopolymer 12, it solidifies the resin. When a layer is fully traced, a movable table 15 is then lowered in the vat 16 of resin. A scanner system 17 directs the laser beam 13 according to a loaded CAD model. The self-adhesive property of the material causes the layers to stick with each other and in this way a three-dimensional part 11 is formed in multi-layers. The stereo lithography process 10 is accurate and suitable for smooth surface finished parts, and may be used for rapid prototyping. Parts manufactured using the stereo lithography process 10 may be used for conceptual designs, product verification, and pattern making. Use of the stereo lithography process 10 may enable the manufacture of ultrasonic inspection reference standards, such as polymer resin reference standards, with varying thicknesses and geometries that resemble the fiber-reinforced part to be inspected. The method of manufacturing an ultrasonic inspection reference standard from a fiber-free polymer resin may not require any tooling, and is not limited to the methods discussed.

To demonstrate the use of a fiber-free photo-polymer resin as a reference standard, a photo-polymer resin reference standard was manufactured in substantially the same configuration as a prior art graphite-epoxy reference standard by using the stereo lithography process 10 shown in FIG. 1. Both standards were then ultrasonically scanned at 5.0 MHz using both the through-transmission technique and the pulse-echo technique. The data obtained when using the through-transmission technique is illustrated in the x-y plot 20 of FIG. 2, while the data obtained when using the pulse-echo technique is illustrated in the x-y plot 30 of FIG. 3. The plots 20 and 30 demonstrate attenuation 22 and 32 measured in decibels (dB) versus thickness 21 and 31 measured in inches. The attenuation is a decrease in intensity of a sound wave as a result of absorption and scattering of ultrasonic energy. The plots 20 and 30 include data points 23 and 33 representing a photo-polymer resin reference standard free of fibers, and data points 24 and 34 representing a prior art graphite-epoxy reference standard.

Figure 2:
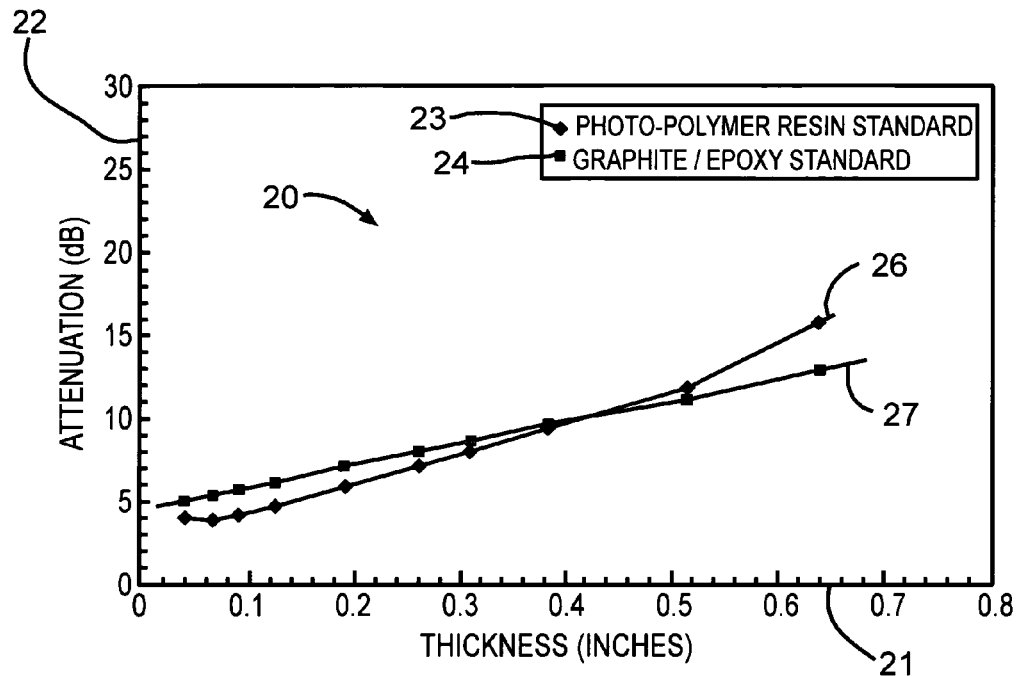
FIG. 2 is an x-y plot showing attenuation versus thickness when applying through-transmission technique to both a photo-polymer resin standard and a graphite-epoxy standard.
Figure 3:
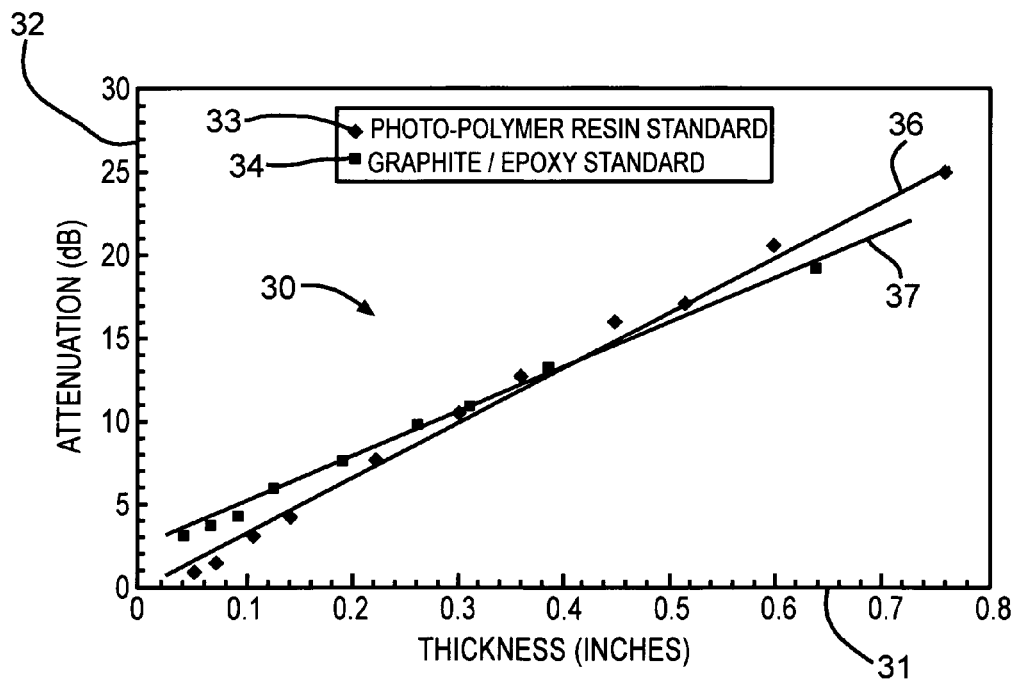
FIG. 3 is an x-y plot showing attenuation versus thickness when applying pulse-echo technique to both a photo-polymer resin standard and a graphite-epoxy standard.

As shown in FIGS. 2 and 3, the slopes 26 and 36 of the photo-polymer resin standard are steeper than the slopes 27 and 37 of the prior art graphite-epoxy reference standard. However, the results are within the system noise, which is typically +/−2 dB. Consequently, the prior art graphite-epoxy reference standard may be substituted with the fiber-free photo-polymer resin reference. Since ultrasonic attenuation is material dependent, the thickness of the polymer resin reference standard may be altered to bring the slopes 26, 27, 36, and 37 in line if needed. Using this approach, a fiber-free polymer resin reference standard may be designed to have an equivalent thickness based on the material properties of the fiber-reinforced composite part to be tested rather than the actual thickness of a prior art fiber-reinforced composite reference standard.

Figure 4:
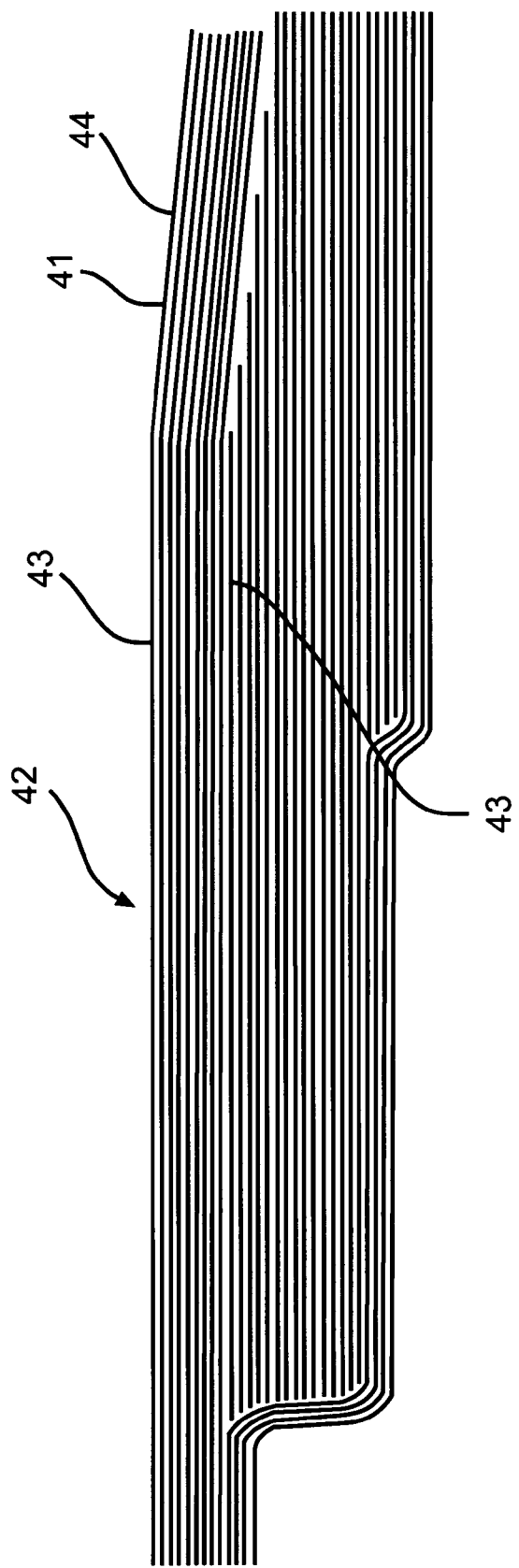
FIG. 4 is a side view of a ply drop (tapered region) of a composite laminate.

The SLA process may produce reference standards with similar acoustic properties to graphite epoxy. This type of standard may be employed when inspecting flat or relatively flat composite laminates. However, this type of standard may have limited application for complex shaped composite laminates that employ ply drops or tapered regions. FIG. 4 shows a ply drop (tapered region) 41 in a composite laminate 42 made of a plurality of graphite plies 43. The ply drop 41 produces an exterior surface 44 which is tapered rather than flat, and as a result, the ply drop 41 will necessarily be aligned at a non-normal angle to an ultrasonic signal when scanned.

It has been discovered that many variables may affect and prohibit accurate inspection of tapered regions in composite laminates. These variables may be due to a loss of energy in the tapered region that are difficult to account for in a flat reference standard. Amongst others, these variables may include the incident angle of the ultrasonic signal as it is scanning the tapered region, the orientation of the tapered region when it is being scanned, the inspection methodology utilized to scan the tapered region, the configuration of the tapered region, and porosity in the tapered region.

Figure 5:
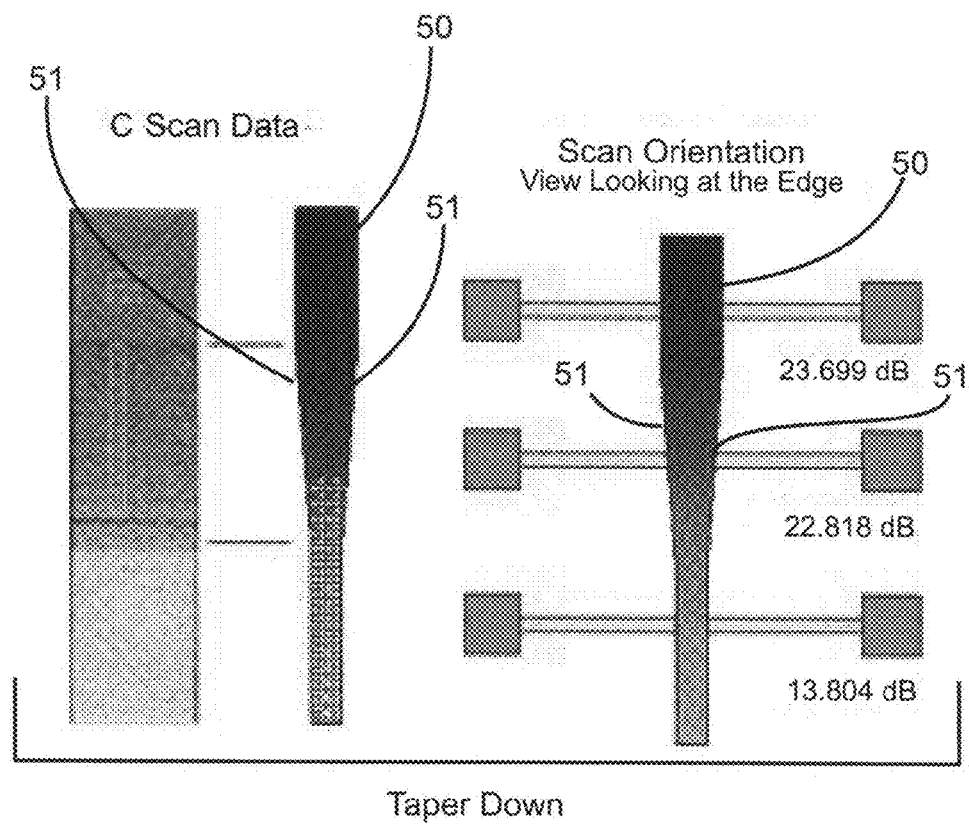
FIG. 5 illustrates an ultrasonic signal response resulting from through-transmission squirter inspection of a dual tapered composite laminate.
Figure 6:
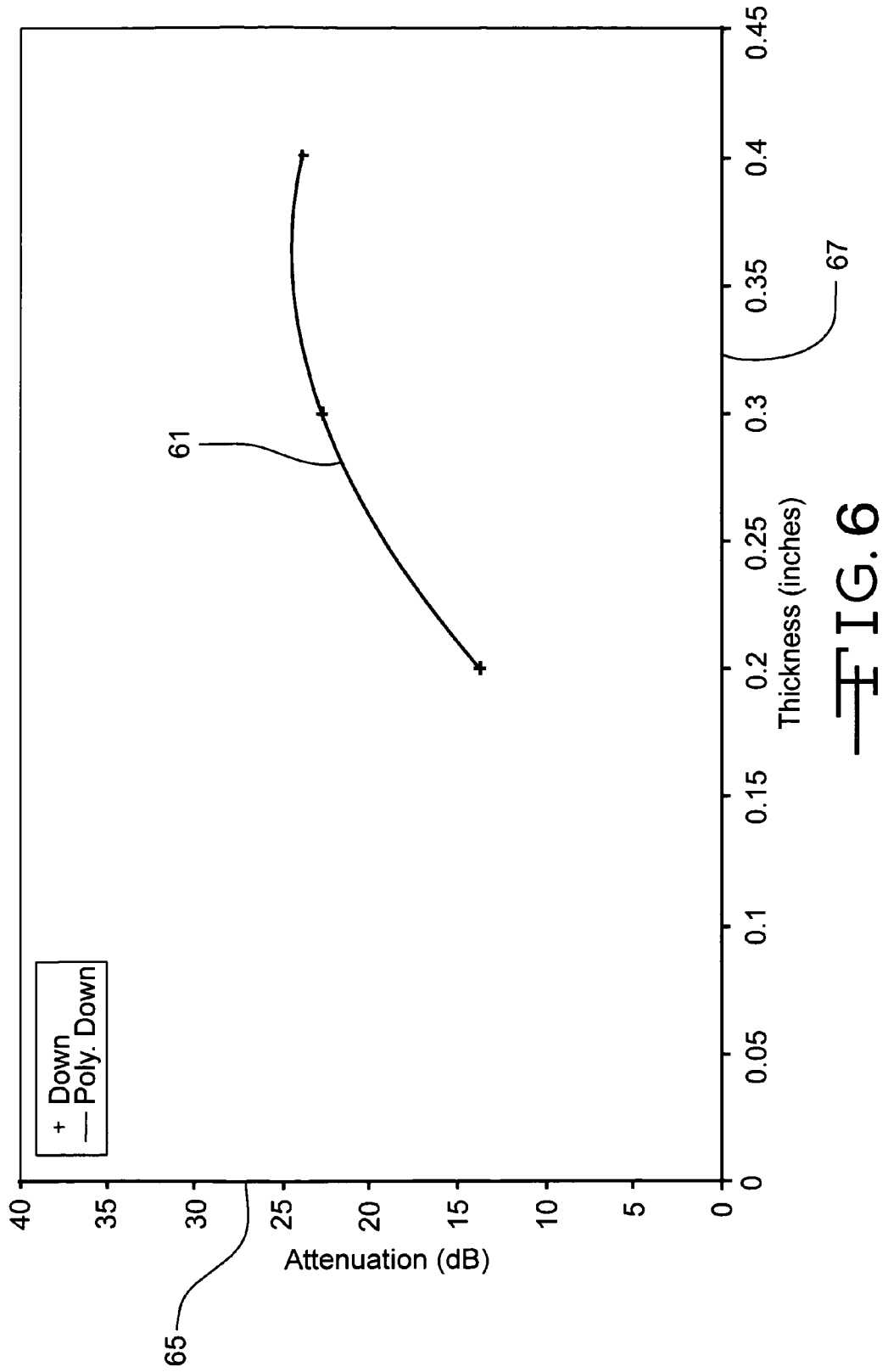
FIG. 6 is an x-y plot showing attenuation versus thickness using the attenuation data of FIG. 5.

As mentioned, one of the variables which may affect inspection of tapered regions in composite laminates is the incident angle of the ultrasonic signal as it is scanning the tapered region. Ultrasonic signals that have an incident angle normal to the part surface produce the lowest energy loss as the sound passes through the part. Non-normal incident angles, like those in tapered regions, may reflect some energy and transmit the remaining energy to produce a higher level of ultrasonic attenuation. The amount of energy transmitted is typically measured in decibels. FIG. 5 illustrates the ultrasonic signal response resulting from the use of through-transmission (UT/TTU) squirter inspection on a dual tapered composite laminate 50. As shown, there is an energy loss in the tapered region 51. The energy loss is due in part to material induced attenuation as well as attenuation resulting from the incident angle of the ultrasonic beam. As depicted, the higher the ultrasonic attenuation the darker the shade of gray. FIG. 6 illustrates the attenuation data 65 from FIG. 5 plotted as a function of laminate thickness 67. As can be seen in the plot, the data is not linear, and the tapered region 61 has a higher level of attenuation than expected due to the incident angle resulting from the tapered region 61.

Figure 7:
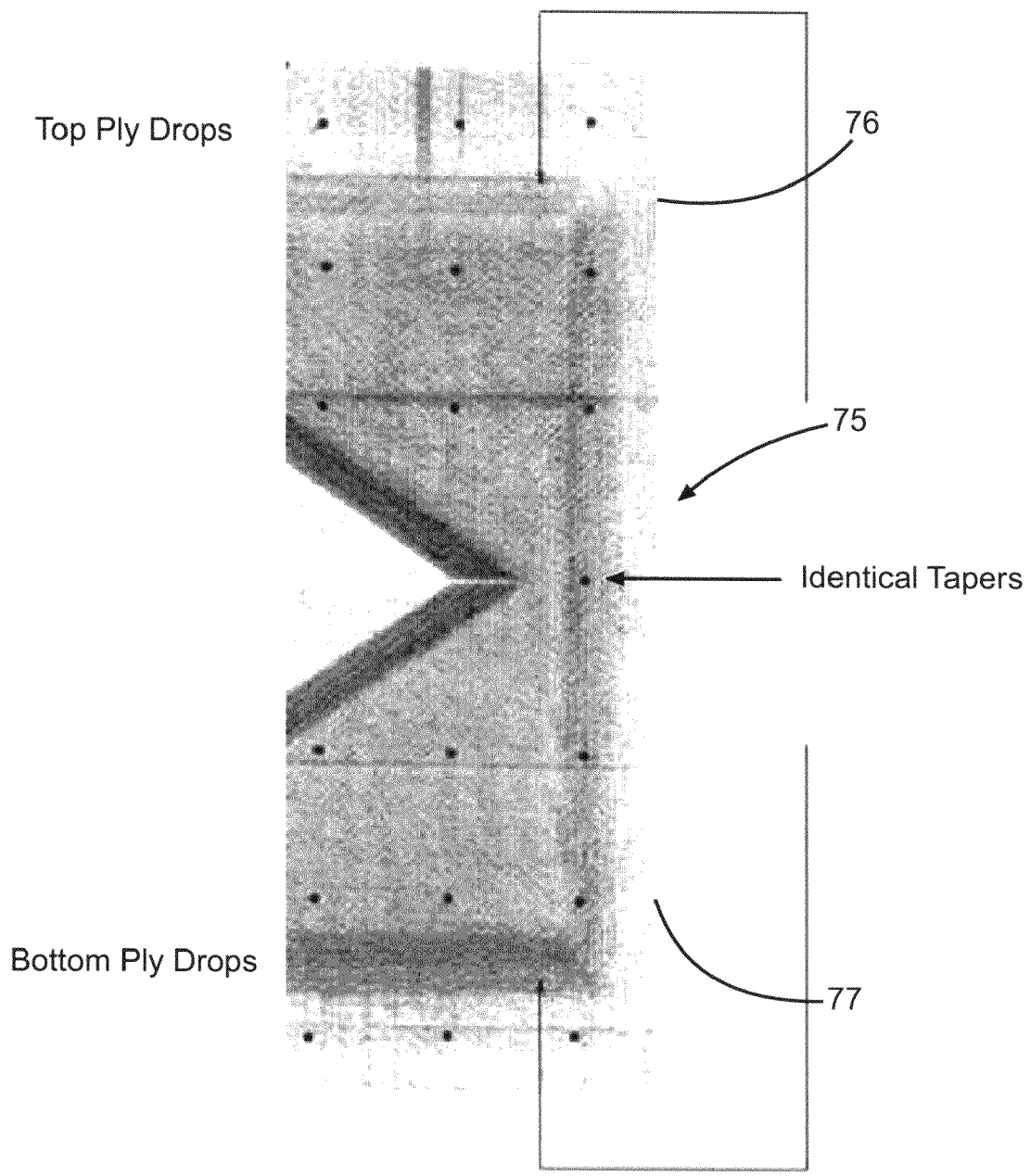
FIG. 7 depicts one embodiment of a composite laminate having identical ply drops on each side.
Figure 8:
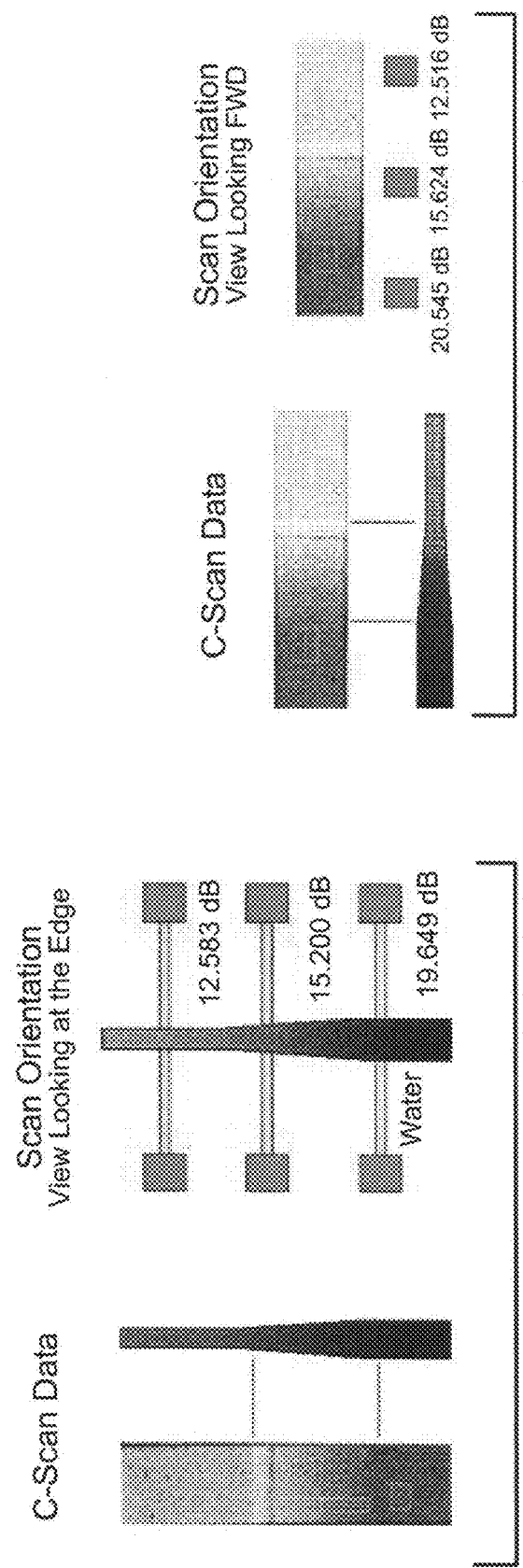
FIG. 8(A) depicts C-scans resulting when a graphite-epoxy tapered part was scanned in an upwardly orientation.
FIG. 8(B) depicts C-scans resulting when a graphite-epoxy tapered part was scanned in a sideways orientation.
Figure 9:
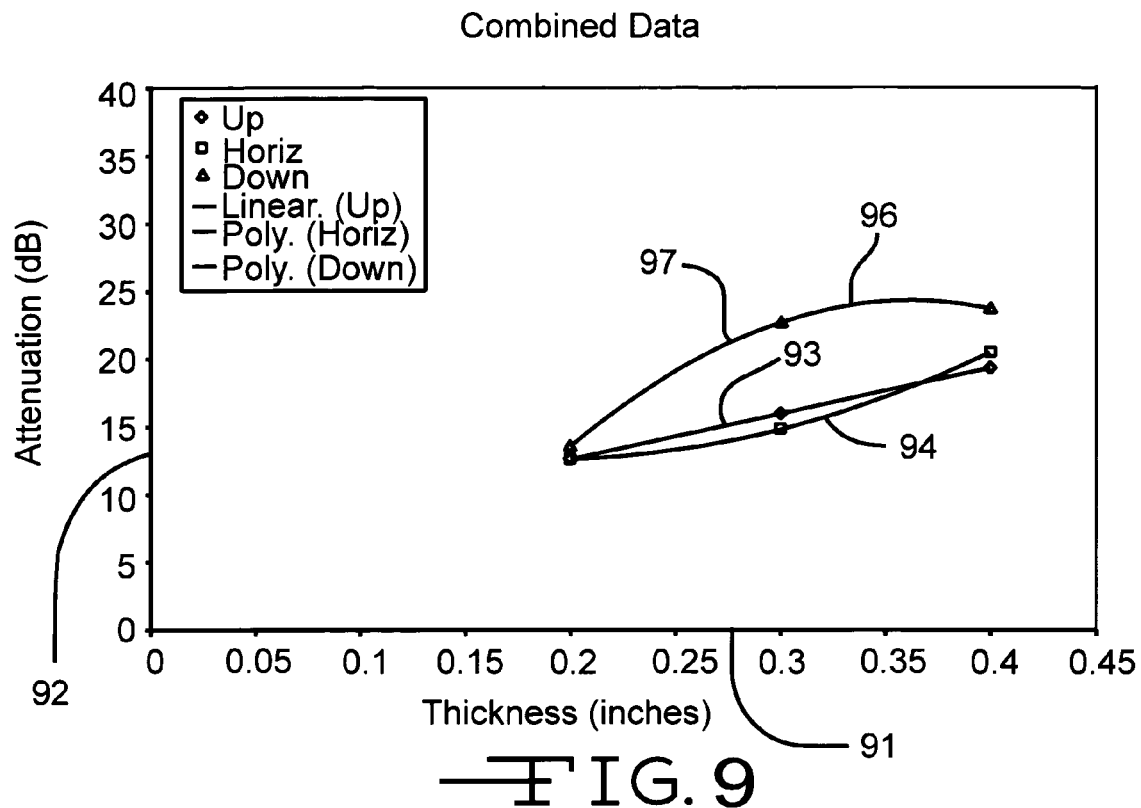
FIG. 9 is an x-y plot showing attenuation versus thickness resulting when a graphite-epoxy tapered part was scanned in upwardly, sideways, and downwardly orientations.

Another of the variables which may affect inspection of tapered regions in composite laminates is the orientation of the tapered region in relation to the scan, which may affect the bulk attenuation of the ultrasonic signal. To illustrate this, the composite laminate 75 shown in FIG. 7, having identical ply drops on each side 76 and 77, was scanned using a traditional squirter type through-transmission (TU/TTU) system. The result was that the ultrasonic attenuation of the top ply drops 76 was lower than the attenuation of the bottom ply drops 77. To graphically illustrate this phenomenon, a graphite epoxy tapered sample was scanned with the taper up, down, and sideways. Histograms were collected and plotted for each scan orientation. FIG. 8(A) illustrates the resulting C-scans for the up orientation. FIG. 8(B) illustrates the resulting C-scans for the sideways orientations. FIG. 9 depicts a plot of the thickness 91 versus attenuation 92 for the up orientation 93, sideways orientation 94, and down orientation 96. As can be seen, the up 93 and sideways 94 data are similar. However, the down data 96 has a much higher attenuation in the tapered region 97. This illustrates why it may be important to have tapered reference standards that substantially match the orientation of the part under inspection.

Yet another of the variables which may affect inspection of tapered regions in composite laminates is what inspection methodology is utilized. Most composite laminates are inspected using squirter type ultrasonic systems at frequencies ranging from 500 KHz to 10 MHz. Squirter type systems may have water column diameters ranging from 0.125" to over 0.375" depending on the application. These systems may employ transducers ranging in size from 0.5" to 1.0" with varying focal lengths from flat to 2". Composite laminates may also be inspected using immersion type systems having backwalls or reflector plates. Which geometric variables and inspection methods are utilized may affect the resulting ultrasonic attenuation when inspecting tapered regions of composite laminates. These variables may make it difficult to apply a universal correction factor to tapered region data when interpreting ultrasonic data in these areas.

Figure 10:
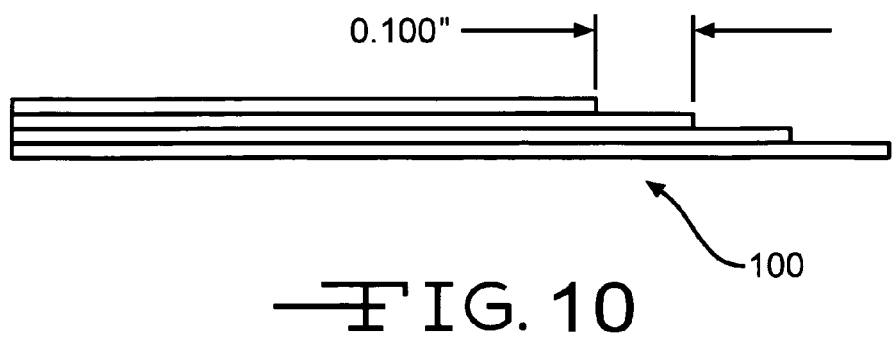
FIG. 10 depicts a composite laminate having a 0.010" per ply thickness.

Another of the variables which may affect inspection of tapered regions in composite laminates is the configuration of the tapered region. Design engineers may try to maximize their designs by introducing ply lay-ups that meet strength requirements, but enable the reduction of weight through removal of unnecessary material. Ply drops are often referred to as being the ratio of ply length to ply thickness. For example, as illustrated in FIG. 10, if a laminate 100 has a per-ply thickness of 0.10" and a ply drop ratio of 10:1, the laminate 100 drops a ply every 0.1". The lower the ratio, the more quickly the plies terminate within the laminate 100. Ply drops which are designed and built to a 5:1 ratio may be more difficult to inspect than ply drops which are built to a 10:1 ratio. The number of plies dropped in a laminate may also affect the difficulty of the inspection. Laminates that drop less plies may be easier to inspect, because as more plies are dropped, the delta thickness differential between the thick area of the laminate and the thin area of the laminate may increase.

Another variable which may affect the inspection of tapered regions in composite laminates is porosity in the tapered region. The addition of porosity in tapered regions may compound the inspection and interpretation of laminates due to the difficulty in manufacturing a reference standard displaying porous properties. Since some graphite/epoxy laminates have very tight levels of acceptance, it may be necessary to produce a reference standard which accurately mimics the porous properties of the part being inspected.

The present invention relates to tapered reference standards, and methods for their manufacture and use, which may substantially mimic the effect porosity has on ultrasonic sound as it passes through a tapered composite laminate. In an embodiment of the invention, an ultrasonic inspection reference standard may be manufactured using stereo lithography on a polymer resin to make a member comprising at least one tapered section. The reference standard may exhibit similar acoustic properties to a tapered composite laminate (fiber/resin combination) to be inspected. In other embodiments, varying types of fiber-free polymer resin may be utilized, including the utilization of a polymer resin which is substantially similar to the resin of a composite material to be inspected. In still other embodiments, a non-stereo lithography process may be applied. In other embodiments, the tapered reference standard may comprise a tapered member which is defined by a plurality of holes, or which is defined by one or more openings in which one or more discrete wires or meshes are disposed. In such manner, the tapered reference standard may be utilized to inspect porous, tapered composite parts.

In one embodiment of the invention, an ultrasonic inspection process starts with designing and building a three-dimensional model of the standard, according to a tapered, fiber-reinforced composite part to be inspected. The tapered, fiber-reinforced composite part to be inspected may comprise a graphite epoxy composite material having a tapered section. The three-dimensional model may be designed to include at least one tapered section to substantially mimic the ultrasonic material properties of the tapered, composite part to be inspected. The tapered section of the model may be predetermined prior to manufacture of the standard in order to provide the standard with at least one of the acceptable and rejectable ultrasonic properties of the tapered, fiber-reinforced composite part to be inspected. In such manner, the designed reference standard may substantially comprise the ultrasonic properties of a fiber-reinforced, tapered, composite part. The tapered section may be designed to be located in varying locations in the model, and may comprise varying sizes, shapes, orientations, configurations, and tapers.

Figure 11:
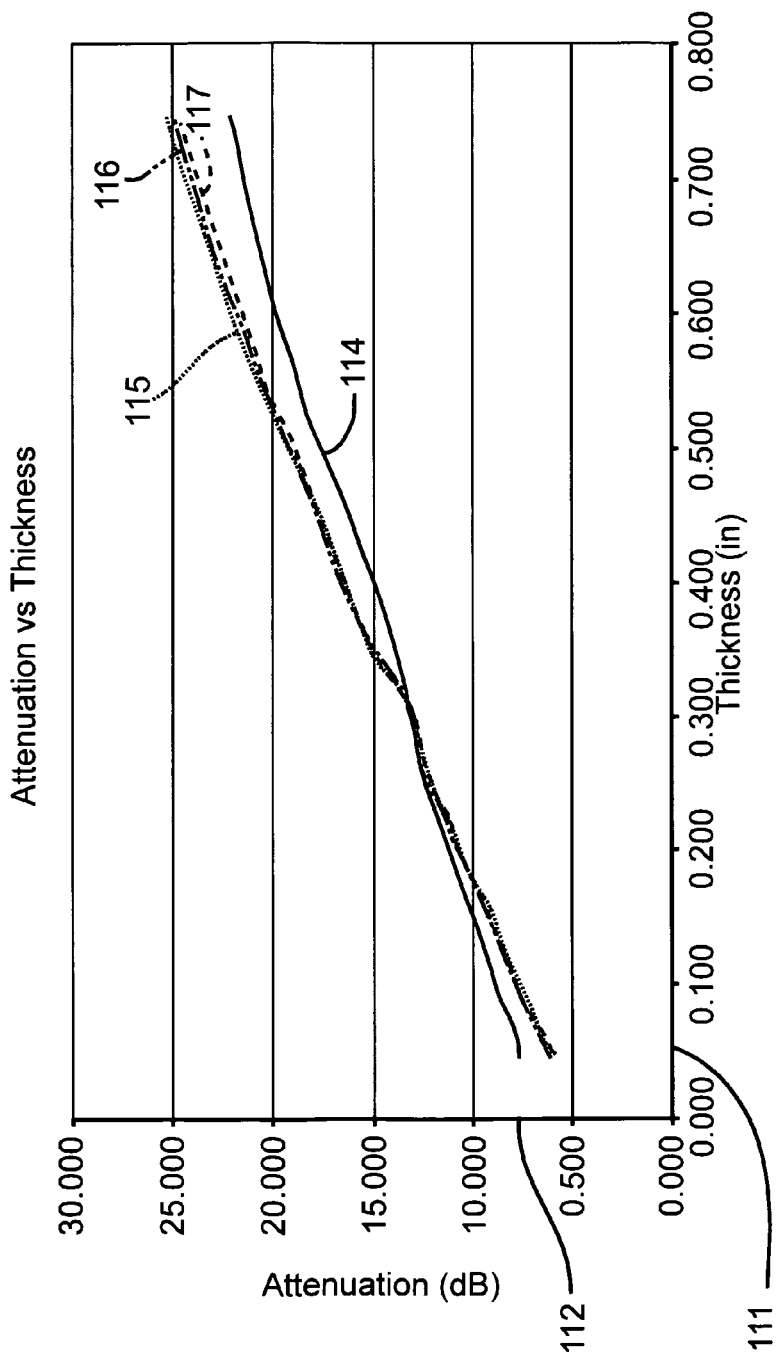
FIG. 11 is an x-y plot showing attenuation versus thickness for a carbon-epoxy standard and three standards produced using SLA to mimic the carbon-epoxy standard.

Because there may be a difference in the ultrasonic attenuation of the part to be inspected, and the attenuation of the resin of which the reference standard may be manufactured, an offset thickness for the model may be determined in order to substantially provide the model with the equivalent ultrasonic attenuation of the part to be inspected. An example of the process which may be used to determine an offset thickness is shown in FIG. 11, which depicts a plot of thickness 111 versus attenuation 112 for a carbon-epoxy standard 114 and three different standards 115, 116, and 117 all produced using SLA on a photopolymer resin to mimic the carbon-epoxy standard 114. By applying a linear regression to determine the slope and intercept of the three SLA standards 115, 116, and 117, a formula can be used to determine the offset thickness of the SLA standard by applying the graphite-epoxy attenuation for a given thickness as depicted by the plot. The model, which may be arrived at using computer-aided-drafting, may be loaded into a stereo lithography machine to manufacture the reference standard by curing a photopolymer resin with a laser. In other embodiments, varying types of resins, such as a fiber-free polymer resin, and varying types of processes may be used to manufacture the standard.

In curing the photopolymer resin, the laser may raster back and forth curing resin in the areas dictated by the model in order to produce a member having one or more tapered sections as designated by the model. The tapered section may comprise a plurality of thicknesses, and may comprise any size, shape, orientation, configuration, or taper. The tapered section may be a substantially equivalent taper, or thickness, based on the material properties of the tapered, composite material to be inspected. The tapered section may be substantially continuous without the inclusion of stepped surfaces. After the SLA process is completed, the standard may be given a post UV cure to harden the resin and to finish manufacture of the standard.

The process may produce an ultrasonic reference standard comprising a fiber-free polymer resin member having at least one tapered section. FIGS. 12 and 12A, and FIGS. 13 and 13A, respectively depict top and cross-sectional views of varying embodiments of single taper reference standards which may be produced utilizing the invention. Similarly, FIGS. 14 and 14A, and FIGS. 15 and 15A, respectively depict top and cross-sectional views of varying embodiments of dual taper reference standards which may be produced utilizing the invention. FIG. 16 depicts a top view of another embodiment of a reference standard under the invention, which may have a single or dual taper. In other embodiments, the invention may produce a reference standard having one or more tapers of varying configurations, shapes, orientations, and sizes. The manufactured standard may substantially mimic the ultrasonic properties of tapered, composite materials, allowing the replacement of a fiber-reinforced composite reference standard. A varying amount of attenuation may be produced in the standard to accomplish the desired ultrasonic reference standard.

The manufactured standard may be used to inspect a tapered, fiber-reinforced, composite part using an ultrasonic technique. For instance, the manufactured standard may be ultrasonically scanned using ultrasonic inspection, such as pulse-echo and through-transmission. A tapered, fiber-reinforced composite part may be ultrasonically scanned using the same technique. The data obtained from scanning the tapered, fiber-reinforced, composite part may be compared with the data obtained from scanning the manufactured standard. Based on the data, a decision may be made as to whether to accept or reject the tapered, composite part.

The invention may produce a tapered reference standard which may be manufactured at lower manufacturing cost, which may be manufactured in less time, and which may be manufactured using a method which does not require any tooling, as compared to many existing tapered, fiber-reinforced composite reference standards. The manufactured tapered, ultrasonic inspection reference standard may substantially comprise the ultrasonic properties of a tapered, graphite-epoxy reference standard or other type of tapered reference standard made of varying materials. In such manner, the manufactured, tapered, ultrasonic inspection reference standard may replace a tapered, graphite-epoxy reference standard, or other type of tapered fiber-reinforced reference standard.

Using stereo lithography to produce index standards comprising tapered members may be of value because manufacturing costs may be roughly ten percent of the traditional cost of manufacturing composite standards with similar tapers. The ability to produce tapers in particular sizes, shapes, orientations, configurations, and tapers may make this approach desirable in the manufacturing of tapered reference standards. Additionally, the nature of the manufacturing process, including its tailorability and repeatability, may enable the production of large numbers of tapered reference standards having substantially equivalent acoustic properties to allow inspection of tapered, composite parts around the world. The cost of manufacturing and certification of reference standards may be reduced through use of the invention. The process may become the foundation for the development of tapered reference standards to characterize ultrasonic equipment, and may replace current tapered, composite reference standards, such as graphite-epoxy, tapered reference standards. The invention may be used for ultrasonic inspection of tapered, composite parts used in the aircraft industry, both commercial and defense, and in other non-aircraft applications.

It should be understood, of course, that the foregoing relates to exemplary embodiments of the invention and that modifications may be made without departing from the spirit and scope of the invention as set forth in the following claims.

We claim:

1. An ultrasonic inspection reference standard for composite materials having at least one first tapered section comprising:
   a member having at least one second tapered section, said member being dual-tapered with a general axis of both of the dual-tapers being parallel to one-another;
   wherein said member is manufactured from a multiple-layered polymer resin using a stereo lithography process.

2. The ultrasonic inspection reference standard of claim 1, wherein said polymer resin is at least one of a photo-polymer resin or fiber-free.

3. The ultrasonic inspection reference standard of claim 2, wherein said polymer resin is both a photo-polymer resin and fiber-free.

4. The ultrasonic inspection reference standard of claim 1, wherein said polymer resin is substantially similar to the resin of the composite material to be inspected.

5. The ultrasonic inspection reference standard of claim 1, wherein said second tapered section comprises a plurality of thicknesses.

6. The ultrasonic inspection reference standard of claim 1, wherein said member is created using a 3D computer-aided-design model.

7. The ultrasonic inspection reference standard of claim 1, wherein at least one thickness of said member is a substantially equivalent thickness based on material properties of said composite material to be inspected.

8. The ultrasonic inspection reference standard of claim 7, wherein said second tapered section in said member comprises substantially equivalent thicknesses based on material properties of the first tapered section in said composite material to be inspected.

9. The ultrasonic inspection reference standard of claim 1, wherein said reference standard contains at least one of the acceptable and rejectable ultrasonic properties of a composite material having at least one first tapered section.

10. The ultrasonic inspection reference standard of claim 9, wherein the taper of said second tapered section is predetermined prior to manufacture of said reference standard to provide said reference standard with at least one of the acceptable and rejectable ultrasonic properties of the composite material.

11. The ultrasonic inspection reference standard of claim 1, wherein said member contains at least one of the acceptable and rejectable ultrasonic properties of a composite material comprising graphite epoxy.

12. The ultrasonic inspection reference standard of claim 1, wherein said member contains at least one of the acceptable and rejectable ultrasonic properties of a composite material having porosity.

13. The ultrasonic inspection reference standard of claim 1, wherein said second tapered section is substantially continuous without stepped surfaces.

14. The ultrasonic inspection reference standard of claim 1, wherein said multiple-layered polymer resin is made of the same resin.

15. An ultrasonic inspection process for tapered composite materials comprising the steps of:
   manufacturing a reference standard, comprising at least one of a discrete wire or a mesh, and a member, wherein the member has at least one first tapered section, and is manufactured from a multiple-layered polymer resin using a stereo lithography process; and
   inspecting a porous fiber-reinforced composite part having at least one second tapered section with an ultrasonic technique using said reference standard.

16. The ultrasonic inspection process of claim 15, wherein the polymer resin is at least one of a photo-polymer resin or fiber-free.

17. The ultrasonic inspection process of claim 16, wherein said polymer resin is both a photo-polymer resin and fiber-free.

18. The ultrasonic inspection process of claim 15, wherein said first tapered section is predetermined prior to manufacture of said reference standard to provide said reference standard with at least one of the acceptable and rejectable ultrasonic properties of said fiber-reinforced composite part.

19. The ultrasonic inspection process of claim 15, wherein said first tapered section of said member is manufactured to comprise substantially equivalent thicknesses based on material properties of said second tapered section in said composite part to be inspected.

20. The ultrasonic inspection process of claim 15, further comprising the steps of:
ultrasonically scanning said reference standard using an ultrasonic inspection technique;
ultrasonically scanning said fiber-reinforced composite part using said ultrasonic inspection technique; and
comparing data obtained from scanning said fiber-reinforced composite part with data obtained from scanning said reference standard.

21. The ultrasonic inspection process of claim 20, further comprising the step of deciding whether to accept or reject said fiber-reinforced composite part based on said data.

22. The ultrasonic inspection process of claim 15, further comprising the steps of:
creating a 3D CAD model of an ultrasonic inspection standard; and
manufacturing said member from a photo-polymer resin.

23. The ultrasonic inspection process of claim 15, further comprising the step of using an ultrasonic technique selected from the group consisting of pulse-echo technique and through-transmission technique to scan said reference standard and to scan said fiber-reinforced composite part.

24. The ultrasonic inspection process of claim 15, further comprising the steps of:
manufacturing said member from a fiber-free photo-polymer resin using the stereo lithography process; and
replacing a fiber-reinforced composite reference standard with said manufactured reference standard.

25. The ultrasonic inspection process of claim 15, wherein said multiple-layered polymer resin comprises the same resin.

26. The ultrasonic inspection process of claim 15, wherein said member is manufactured to be dual-tapered with a general axis of both of the dual-tapers being parallel to one-another.

27. An ultrasonic inspection reference standard for composite materials having at least one first tapered section comprising:
a member having at least one second tapered section, wherein said member is manufactured from a polymer resin, and said ultrasonic reference standard is for composite materials having porosity; and
at least one of a discrete wire or a mesh.

28. The ultrasonic inspection reference standard of claim 27, wherein said polymer resin is fiber-free.

29. The ultrasonic inspection reference standard of claim 27, wherein said polymer resin is a photo-polymer resin.

30. The ultrasonic inspection reference standard of claim 27, wherein said polymer resin is multiple-layered.

31. The ultrasonic inspection reference standard of claim 30, wherein said multiple-layered polymer resin is made of the same resin.

32. The ultrasonic inspection reference standard of claim 27, wherein said member is dual-tapered with a general axis of both of the dual-tapers being parallel to one-another.

33. The ultrasonic inspection reference standard of claim 27, wherein said ultrasonic inspection reference standard comprises the discrete wire.

34. The ultrasonic inspection reference standard of claim 27, wherein said ultrasonic inspection reference standard comprises the mesh.

* * * * *